United States Patent [19]

Saville

[11] Plant 4,471

[45] Oct. 30, 1979

[54] ROSE PLANT

[76] Inventor: F. Harmon Saville, 58 Hammond St., Rowley, Mass. 19669

[21] Appl. No.: 955,223

[22] Filed: Oct. 27, 1978

[51] Int. Cl.[2] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose of salmon coloring underlaid with light yellow but displays different color on aging depending on whether grown indoors or outdoors.

7 Drawing Figures

1

The present invention relates to a new and distinct variety of rose plant of the miniature rose class, which was originated by my crossing as seed parent the rose known as "Sheri Anne" and the rose known as "Watercolor" as pollen parent.

Among the novel characteristics possessed by this new variety which distinguish it from its parents and all other varieties of which I am aware are strikingly colored blooms which differ greatly on indoor and outdoor grown plants and a compact moderately spreading plant. The flowers are colored salmon underlaid with light yellow but if grown indoors the flowers, upon aging, lighten substantially to off-white with pink tone whereas when grown outdoors the salmon color deepens and becomes more intense, spreading to petal areas exposed to the sun. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of salmon coloring underlaid with light yellow borne both singly and in sprays having as many as ten or more blooms delightfully displayed on a compact, moderately spreading plant. The flowers are usually well formed and are of a novel coloring, varying under different light conditions, strikingly different indoor and outdoor grown. The blooms are high centered and the plant is very floriferous. The petals are thick with heavy substance. The plant itself is attractive and very vigorous, abundant foliage with well branching growth.

The accompanying drawings show typical specimens of the vegetative growth and flowers of the new variety in different stages of development and as depicted in color as nearly true as it is reasonably possible to make the same in color illustrations of this character.

The following is a detailed description of my new variety, with color terminology in accordance with the Royal Horticultural Society Color Chart (RHSCC). The terminology used in color description herein refers to plate numbers in the aforementioned color chart, e.g., "40A" is plate 40A of the Royal Horticultural Society Color Chart.

Parentage: Seedling.

2

*Seed parent.*—"Sheri Anne".

*Pollen parent.*—"Watercolor".

Class: Miniature.

Figure 1:
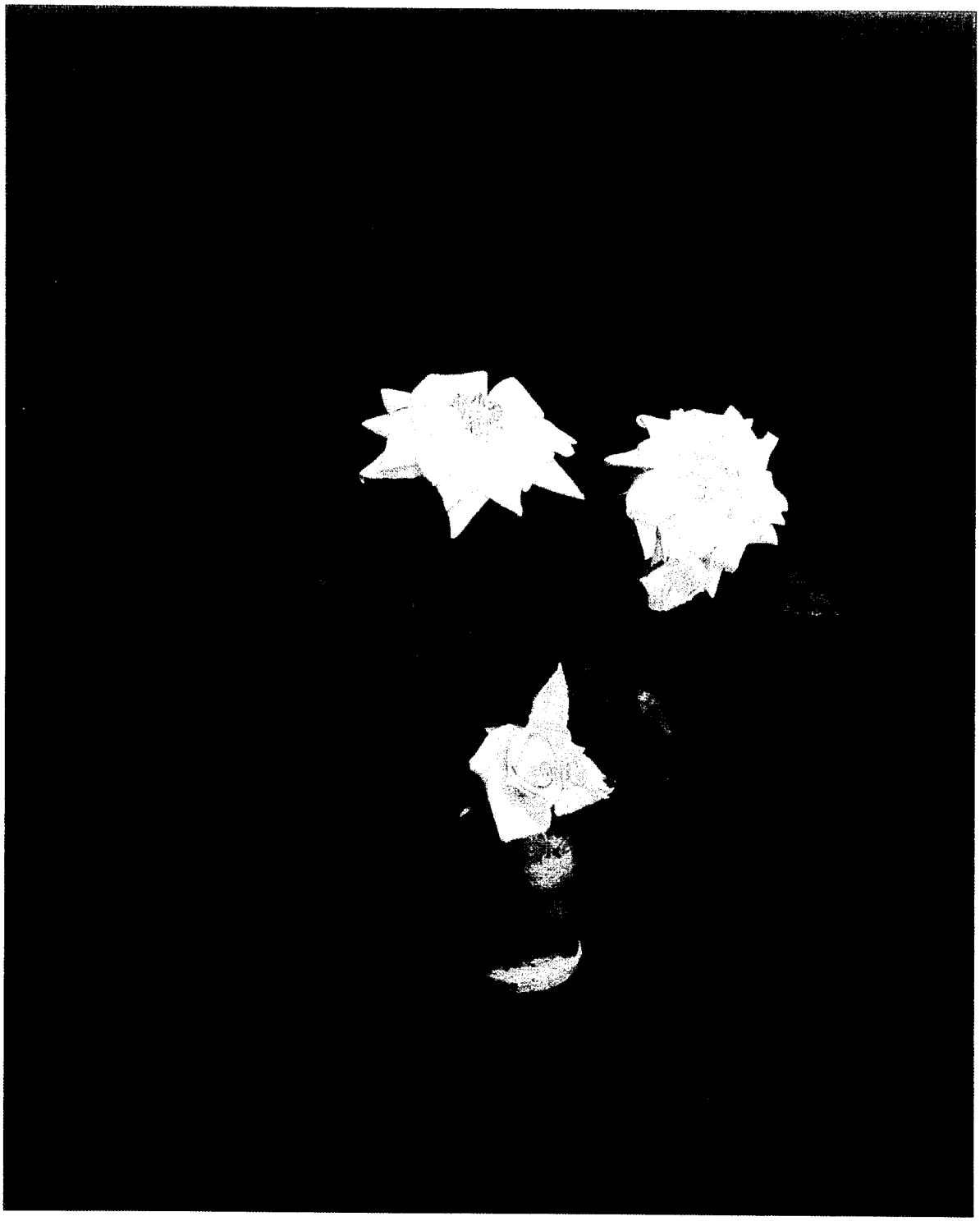
FIG. 1 is an illustration showing flowers from plants grown indoors.
Figure 2:
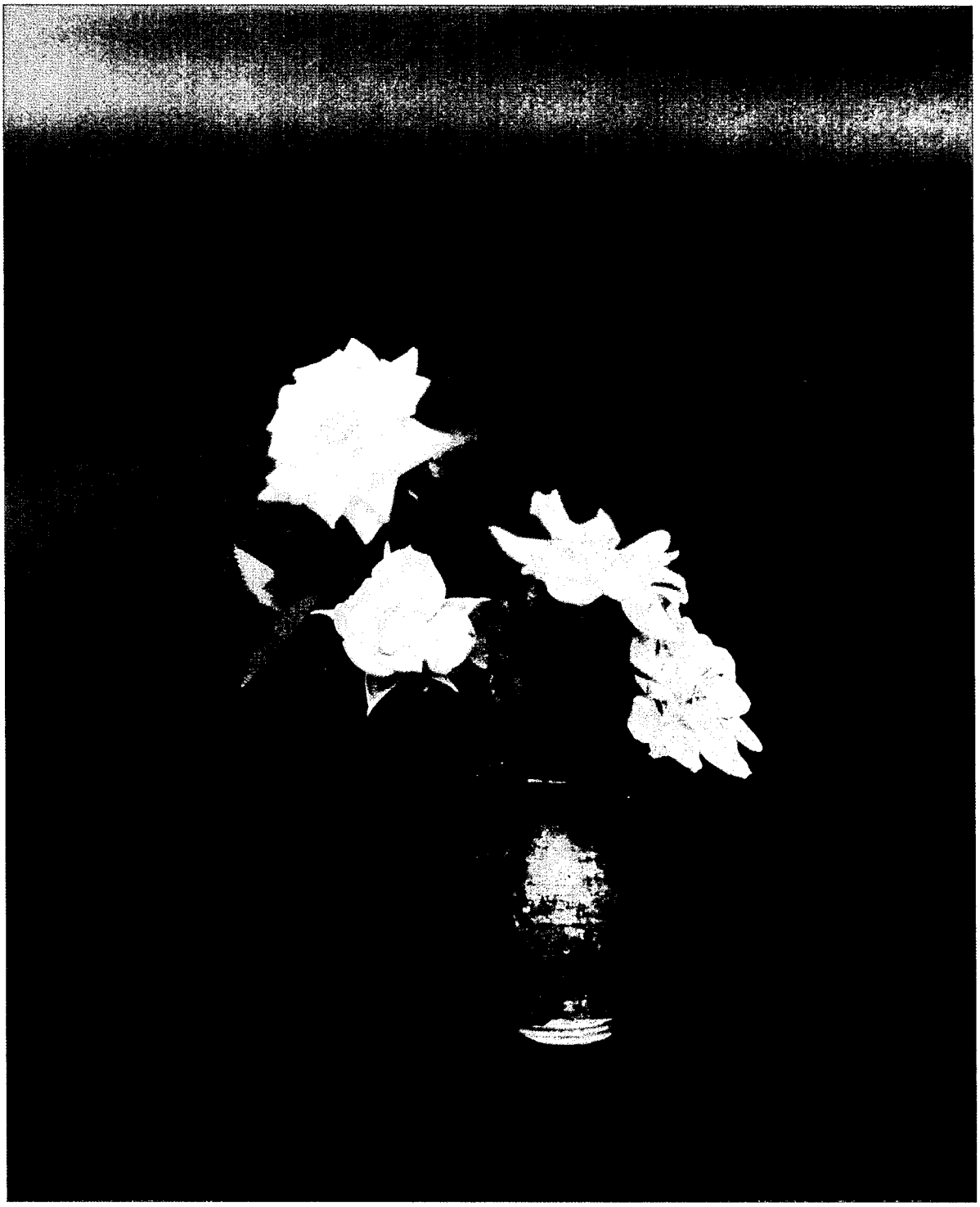
FIG. 2 is an illustration showing flowers from plants grown outdoors exposed to sun.

The following observations are made of specimens grown both indoor, referring to FIG. 1, and outdoor, referring to FIG. 2, in Essex County, Mass., during the month of August.

I. FLOWER

Blooming habit: Continuous.

A. Bud:

(1) *Size.*—Medium.

(2) Form.—Ovate, pointed.

(3) *Color.*—When sepals first divide — 50A to 50B, base — 8C.

(4) *Sepals.*—Slightly foliated, bronze in sun, longer than bud, usually one of the sepals is longer and more foliated than the others.

(5) *Peduncle.*—Length — normal to short. Aspect — straight. Strength — erect, strong. Color — 184B in sun; 142B in shade (same peduncle).

B. Bloom:

(1) *Size.*—Average size when fully expanded — about 1½ to 1¾ inches.

(2) *Borne.*—Both singly and in sprays sometimes ten or more blooms in cluster.

(3) *Form.*—High centered blooms, becoming flat upon opening, petals at first loosely rolled outward becoming strongly reflexed upon maturity.

(4) *Petalage.*—Number of petals under normal conditions — about 27 to 30.

(5) *Color.*—FIG. 2 (indoor grown): When sepals begin to unfurl color at base is 8C petals are tipped 50B, inside base of petals may be 8B tipped and lightly blended with 50C to 50D on inside and 6D tipped and lightly blended with 50C and 50D on outside as flower becomes half-blown; general tonality from distance is yellow to yellow-white center with pink tips and slight pink flushing. As bloom ages the color changes to 8D base with 50C, on inside; the general tonality is pale yellow center with pink tips. After three or more days inside and outside are essentially the same: 155D with pronounced petal edge coloring (outline) 50C. FIG. 1 (outdoor grown): When petals begin to unfurl — upper side of innermost petals are 19C; when half blown — inside of petals 18A to 18D flushed with 39B and reverse side of petals 11D flushed with 41B; after first two days the petal inner surface is 36D and at center of flower 10D and outer petals 18D flushed with 42A, base of petals 11D and reverse of petals 11D flushed with 41B, the general tonality being pale pink. As bloom ages salmon coloring becomes paler; general tonality becomes pink and cream.

C. Petals:
(1) *Texture.*—Thick, heavy substance.
(2) *Appearance.*—Inside — satiny with texture. Outside — satiny and smooth.
(3) *Form.*—Ovate.
(4) *Arrangement.*—Regularly arranged, shingle-like.
(5) *Petaloids in center.*—Few.
(6) *Persistence.*—Drop off cleanly after lasting well.
(7) *Fragrance.*—Slight, sweet.
(8) *Lasting quality.*—Very long lasting on plant and when cut.

2. REPRODUCTIVE ORGANS

A. Stamens, filaments and anthers:
(1) *Arrangement.*—Regularly arranged around styles.
(2) *Color.*—23B.

B. Pollen: Color — 23B.

C. Styles: Medium, length, normal.

D. Stigmas: Color — 161D.

E. Hips: None observed.

3. PLANT

A. Form: Compact, moderately spreading.

B. Growth: Very vigorous, well branched, bushy.

C. Foliage: Compound 5 to 7 leaflet leaves.
(1) *Size.*—Medium.
(2) *Quantity.*—Abundant, normal to short internodes.

(3) *Color.*—New foliage: Upper side — near to 178A over 137A; Under side — near to 59A. Old foliage: Upper side — 137A; Under side — 137D.
(4) *Shape.*—Pointed, oval.
(5) *Texture.*—Upper side — smooth, slight gloss. Under side — matte.
(6) *Edge.*—Serrated.
(7) *Serration.*—Deeper toward point of leaflet, regular.
(8) *Leaf stem.*—Color — near to 178A. Under side — 143C.
(9) *Stipules.*—Medium long, smooth, long points.
(10) *Resistance to disease.*—Blackspot — good. Mildew — fair. Rust — good.

D. Wood:
(1) *New wood.*—Color — near 184B. Bark — smooth.
(2) *Old wood.*—Color — near to 139C. Bark — smooth.

E. Thorns:
(1) *Thorns.*—Quantity — ordinary. On laterals from stalk — few to none. Form — very long, thin, pointed. Length — medium. Color (when young) — 44D. Position — irregular.
(2) *Prickles.*—None.

F. Winter hardiness: Needs some protection in extreme climates.

I claim:

1. A new and distinct variety of rose plant of the miniature class, substantially as shown and described, characterized particularly by blooms of novel coloring varying under different light conditions, strikingly different indoor and outdoor grown on a very floriferous plant displaying flowers both singly borne and in clusters.

* * * * *